US00PP10082P

United States Patent [19]

Olesen et al.

[11] Patent Number: Plant 10,082

[45] Date of Patent: Oct. 28, 1997

[54] MINIATURE ROSE PLANT NAMED 'POULAVON'

[75] Inventors: Mogens N. Olesen; Pernille Olesen, both of Fredensborg, Denmark

[73] Assignee: Bear Creek Gardens, Inc., Medford, Oreg.

[21] Appl. No.: 605,821

[22] Filed: Feb. 21, 1996

[51] Int. Cl.[6] ..... A01H 5/00

[52] U.S. Cl. ..... Plt./9

[58] Field of Search ..... Plt./7.1, 9

*Primary Examiner*—Howard J. Locker

*Attorney, Agent, or Firm*—Klarquist Sparkman Campbell Leigh & Whinston, LLP

[57] ABSTRACT

A miniature rose having light pink flowers; compact even growth when grown in a pot; long shelf life and being readily propagated by softwood cuttings. It is a flower color mutation of the variety POULfect.

1 Drawing Sheet

The present invention relates to a new and distinct variety of rose plant of the miniature class which was discovered by us as a spontaneous mutation of the variety POULfect, which variety is the subject of co-pending application Ser. No. 08,606,894, filed Feb. 21, 1996. This new mutation was discovered in a greenhouse located in Broby, Denmark in the Spring of 1993.

The parent variety POULfect has salmon colored flowers that are represented by Royal Horticultural Society Colour Chart Red Group 38A. The plant claimed herein has light pink flower color represented by Red Group 36D. In all other respects, the two varieties are the same.

The following unique combination of characteristics are outstanding in the new variety and distinguish it from its parent, as well as from all other varieties of which we are aware:

1. Attractive, nonfading, light pink colored flowers;
2. Long shelf life in bloom;
3. Compact, even growth making it ideal for pot culture; and
4. Ease of propagation from softwood cuttings.

Asexual reproduction of this new variety by softwood cuttings, as performed at Wasco and Somis, Calif., and Fredensborg, Denmark, shows that the flower color mutation and all other characteristics and distinctions come true to form and are established and transmitted through succeeding propagation.

The accompanying illustration shows typical specimens of the flowers of this new variety and of its parent in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage of POULavon: Mutation of POULfect.

Classification:

*Botanical.*—*Rosa hybrida.*

*Commercial.*—Miniature.

FLOWER

Observations made from specimens grown in a greenhouse environment at Somis, Calif., and Fredensborg, Denmark.

Blooming habit: Continuous.

Bud:

*Size.*—⅝ inch long when the petals start to unfurl.

*Form.*—The bud form is short, pointed ovoid.

*Color.*—When sepals first divide, bud color is Red Group 36D. When half blown, the upper sides of the petals are Red Group 36D; and the lower sides of the petals are Red Group 36D.

*Sepals.*—Color: Green Group 138A. Surface texture: Covered in fine hairs. There are three lightly appendaged sepals. There are two unappendaged sepals with hairy edges that also have a few glands.

*Receptacle.*—Color: Green Group 143A. Shape: Funnel. Size: Small (¼"×3/16"). Surface: Smooth.

*Peduncle.*—Length: Short (1½" to 1¾"). Surface: Smooth. Color: Medium green. Strength: Stiff and erect.

Bloom:

*Size.*—Small. Average open size is 1½ inches to 1¾ inches.

*Borne.*—Singly, several together, in pyramidal clusters of 3–5 flowers.

*Stems.*—Short (6"–8") and strong.

*Form.*—When first open: High center. Permanence: Flattens and outer petals curl back.

*Petalage.*—Number of petals under normal conditions: 30–35.

*Color.*—The upper side of the petals is Red Group 36D. The reverse side of the petals is Red Group 36D. The base of each petal has a small (⅛"×⅛") Yellow Group 3D half moon at the point of attachment. The major color on the upper side is Red Group 36D.

*Variegations.*—Occasional greenish streak on the guard petals.

*Discoloration.*—There is no change in the color of the petals until they drop on day 7 or 8.

*Fragrance.*—None.

*Shelf life.*—Under low light urban conditions, potted plant has blooming period of 15 or more days.

Petals:

*Texture.*—Thick and leathery.

*Shape.*—Round to slightly oval.

*Form.*—Tips slightly recurved.

*Arrangement.*—Imbricated, with few petaloids in the center.

*Persistence.*—Drop off cleanly.

*Lastingness.*—On the plant: Long, 7–8 days. As a cut flower: Not tested.

Reproductive parts:

*Anthers.*—Size: Medium. Quantity: Many. Color: Yellow. Arrangement: Regular around styles.

*Filaments.*—Color: White.

*Pollen.*—Color: Lemon yellow.

*Styles.*—Color: Reddish.

*Stigmas.*—Color: White.

Form: Bush.

Growth: Vigorous, dwarf, upright, branching, compact. Plant in a 5 inch container will be 10–12 inches tall.

Foliage: Number of leaflets on normal mid-stem leaves: 5 or 7.

*Size.*—Small (3"–3¼"×2"–2¼").

*Quantity.*—Abundant.

*Color.*—New foliage: Very little anthocyanin. Upper: Green Group 137A. Lower: Green Group 138B with some reddish pigment on the margins of the leaf margins. Old foliage: Upper: Green Group 139A. Lower: Green Group 138B.

Leaflets:

*Shape.*—Pointed oval.

*Texture.*—Upper side: Glossy and smooth.

*Edge.*—Serrated.

*Serration.*—Single and small.

*Petiole rachis.*—Color: Green.

*Petiole underside.*—Smooth with occasional prickles.

*Stipules.*—Short (¼"), serrated, and bearded.

*Disease resistance.*—Resistant to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short (3/16") and straight.

*Color when young.*—Red.

Small prickles:

*Quantity.*—On main stalks: None. On laterals: None.

I claim:

1. A new and distinct variety of rose plant of the miniature class, substantially as herein shown and described, a sport of the variety POULfect characterized particularly as to novelty by its light pink flowers which distinguish it from its parent variety; compact even growth under pot culture; long shelf life; and ease of propagation from softwood cuttings.

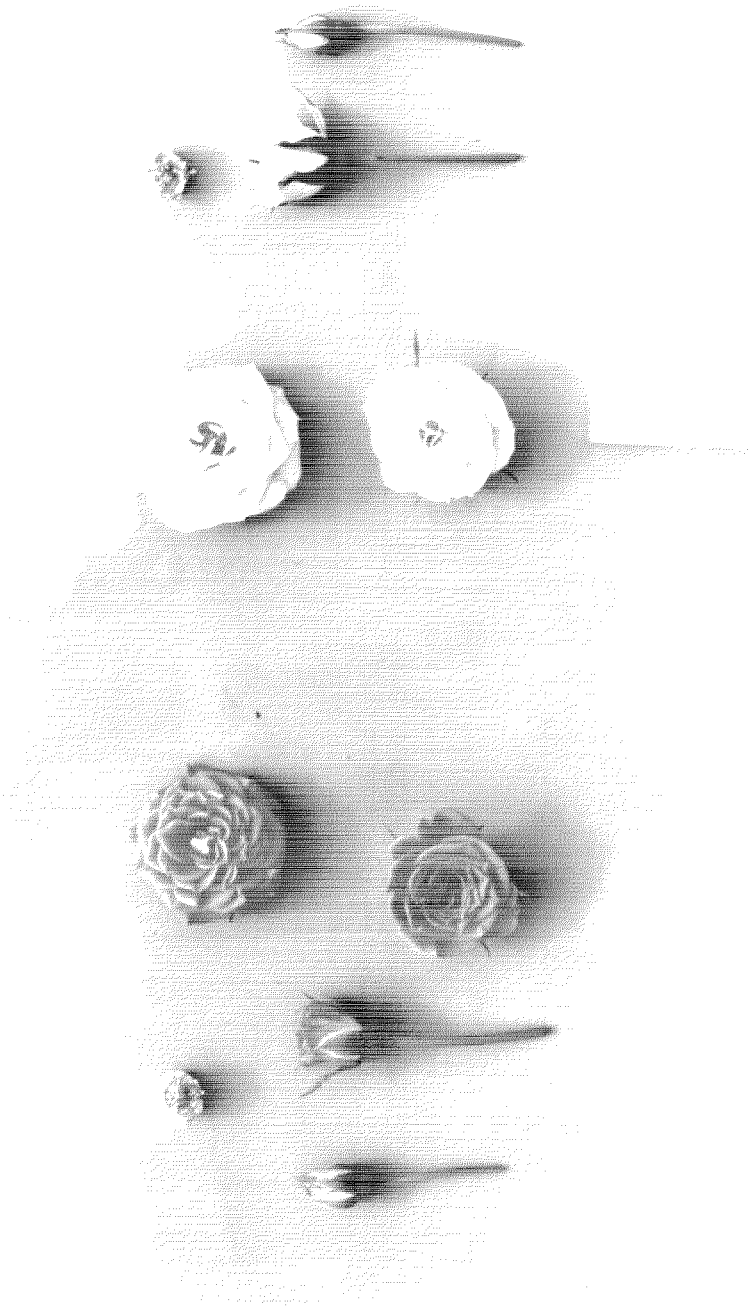

* * * * *